United States Patent [19]

Hanson

[11] Patent Number: 4,687,482
[45] Date of Patent: Aug. 18, 1987

[54] VASCULAR PROSTHESIS

[75] Inventor: Stephen R. Hanson, Encinitas, Calif.

[73] Assignee: Scripps Clinic and Research Foundation, La Jolla, Calif.

[21] Appl. No.: 604,996

[22] Filed: Apr. 27, 1984

[51] Int. Cl.$^4$ ................................................ A61F 1/24
[52] U.S. Cl. .......................................... 623/1; 623/9; 623/12
[58] Field of Search ........................ 3/1.4; 623/1, 9, 12

[56] References Cited

U.S. PATENT DOCUMENTS

| | | | |
|---|---|---|---|
| 3,839,743 | 10/1974 | Schwarcz | 3/1.4 |
| 4,321,711 | 3/1982 | Mano | 3/1.4 |
| 4,377,010 | 3/1983 | Fydelor et al. | 3/1.4 |

FOREIGN PATENT DOCUMENTS

WO80/02641 12/1980 PCT Int'l Appl. ...................... 3/1.4

OTHER PUBLICATIONS

Wilkes et al., "Porous Segmented Polyurethanes—Possible Candidates as Biomaterials", J. Biomed. Mater. Res., vol. 7, pp. 541–554 (1973).

Primary Examiner—John Kight
Assistant Examiner—Kriellion Morgan
Attorney, Agent, or Firm—Dressler, Goldsmith, Shore, Sutker & Milnamow, Ltd.

[57] ABSTRACT

A vascular prosthesis for implantation in a living mammalian body and a method for producing same are disclosed. The vascular prosthesis has a hydrophobic polymeric layer on its luminal surface defining a substantially non-thrombogenic flow surface. The polymeric material of the layer defining the flow surface exhibits a rate of platelet consumption of less than about $20 \times 10^8$ platelets/cm$^2$·day.

32 Claims, 16 Drawing Figures

VASCULAR PROSTHESIS

DESCRIPTION

Technical Field

The present invention relates to vascular prostheses, and more particularly to vascular prostheses having a hydrophobic lining on their luminal surface.

BACKGROUND OF THE INVENTION

Synthetic, small caliber vascular prostheses or grafts, having an inner diameter of 3-5 millimeters, have not been widely used clinically due to the occurence of early thrombotic occlusion, National Institute of Health (NIH) Publication No. 82-1215, December 1981; Mortensen, "Vascular Replacements: A Study of Safety and Performance," NIH Report No. FDA/BMD-81/65 (1981). The clinical data on peripheral arterial reconstruction using either natural or synthetic vascular grafts indicate only a 40-60 percent long term patency rate at best, NIH Publication No. 82-1215, supra. Autogenous saphenous veins are currently considered the preferable graft for small artery replacement, as in coronary bypass surgery, yet a substantial number (20-40 percent) of vein grafts fail during the five year interval following surgery, Whittemore et al., Ann. Surg., 193, 35 (1981). The development of improved grafts is, therefore, of significant clinical importance.

Excluding technical errors and the progression of natural disease, graft failure occurs primarily through two distinct mechanisms. The first is progressive thrombotic occlusion and accumulation of blood elements due to the inherent thrombogenicity of the blood contacting surface. The second and more recently recognized mechanism is neointimal hyperplasia, or progressive stenotic occlusion due to ingrowth of natural tissues, that are primarily smooth muscle cells.

The reactions of blood platelets may contribute significantly to both modes of graft failure. These blood cells are a primary stimulus for the initiation and propagation of thrombus and are a major component of arterial thrombi as determined morphologically. In addition, platelets contain a factor that is mitogenic for smooth muscle cells, Ross et al., Athero. Rev., 3, 69 (1978), and therefore may contribute to the development of initimal hyperplasia. For example, animals given antiplatelet drug therapy in association with vascular grafts develop significantly less stenotic tissue ingrowth than untreated controls, Hagen et al., Ann. Surg., 195, 328 (1982). Also, the earliest platelet reactions postoperatively may markedly increase long term graft patency. In a recent study of 407 patients undergoing coronary bypass grafting, significant late benefit was achieved for periods greater than one year in those patients started on antiplatelet drugs before the operation, as compared to patients given identical agents, but initiated seven hours after the operation, Cheseboro et al., N. Engl. J. Med., 307, 73 (1982). Clearly, reduced platelet thrombus formation is of critical importance for improving the performance of vascular graft materials.

Typically, the physical and chemical properties of synthetic vascular grafts have been dictated by the requirements of the surgical community. These requirements include strength, durability, ease of handling, suturability, and resistance to kinking. Additionally, it has been propounded that the best way to achieve long-term graft patency is to use grafts composed of fabrics or having pores or interstices that allow ingrowth of cellular tissue through the wall of the graft, resulting in a cellular, fibrinous, or collagenous flow surface that might be nonthrombogenic, Sauvage et al., Surg. Clin. N. Am., 54, 213 (1974). Thus, virtually all synthetic vascular grafts in current use are porous or fabric materials (knitted or woven) composed of either Teflon or Dacron. However, the following problems have arisen with such grafts: (1) The chemical composition and "rough" or textured nature of commercial grafts makes them thrombogenic. They actively accumulate platelets and other blood elements. (2) Commercial grafts do not heal completely. Active accumulation of thrombus has been documented as late as nine years after graft placement, Goldman et al., Br. J. Surg., 69, (Suppl.), S38 (1982); Ritchie et al., Am. J. Cardiol., 47, 882 (1981). (3) Even modest cellular ingrowth into the graft lumen may markedly increase the resistance to blood flow. This problem is particularly acute with small caliber grafts, Strandness et al., in Hemodynamics for Surgeons, Grune and Stratton, N.Y., p. 343 (1975).

Currently, polymeric vascular grafts are designed to be porous, exhibiting a fabric or textured blood-contacting surface that allows healing via the migration of vascular tissue cells into, along or through the graft wall. In this manner, the blood-contacting surface will eventually be cellular in nature, and may contribute to luminal thickening.

Progress towards developing improved graft material has been greatly impeded by the lack of suitable animal models. Substantially all work in the area has been performed using dogs. While this species may be suitable for assessing graft healing by tissue ingrowth, it may not be suitable for simulating graft thrombus formation in a manner relevant to human disease, Clagett, "In Vivo Evaluation of Platelet Reactivity with Vasular Prostheses," in Biologic and Synthetic Vascular Prostheses, J. Stanley ed., Grune and Stratton, N.Y., p. 131 (1982). Among nonhuman primates, the baboon appears to be the animal model of choice, Clagett, supra; Hampton et al., J. Appl. Physiol., 21, 1713 (1966); Todd et al., J. Med. Primatol., 1, 132 (1972); Hanson et al., Scanning Electron Microsc., II, 773 (1982); Hanson et al., J. Clin. Lab Med., 95, 289 (1980).

SUMMARY OF THE INVENTION

The present invention contemplates a vascular prosthesis and a method of preparing same. The vascular prosthesis of the present invention can be implanted in a living mammal and comprises (a) an elongated tubular segment having a substantially foraminous, non-compliant, hollow body portion, open at both ends, the hollow body portion having a luminal surface defining a confined-flow passageway, and (b) a hydrophobic, physiologically compatible lining on the luminal surface, which lining defines a thrombus-resistant flow surface. The lining is constituted by a polymeric material exhibiting a rate of platelet consumption of less than about $20 \times 10^8$ platelets/$cm^2$·day.

In one aspect of the present invention, the lining in the vascular prosthesis of the present invention may completely coat the luminal surface of the vascular prosthesis to render the luminal surface substantially smooth. Alternatively, the lining may be a very thin coating that does not substantially alter the texture or morphology of the prosthesis, but only coats the fibers of the luminal surface and subsequently polymerizes around the fibers leaving the fibers essentially unchanged.

In another aspect of the present invention, the lining in the vascular prosthesis is constituted by a plurality of discrete, substantially coextensive polymeric layers, the outermost of which serves as a barrier against possible adsorption of lipids or other blood constituents onto the luminal surface of the prosthesis.

In yet another aspect of the present invention, a method of producing the above described vascular prosthesis having a luminal surface is contemplated. The method comprises (a) depositing a polymeric material onto the luminal surface; and (b) polymerizing said polymeric material to form a hydrophobic lining on the luminal surface. If desired, a substantially smooth flow surface may be so produced.

The method may also include depositing an outermost polymeric layer onto the luminal surface of the above described vascular prosthesis by glow discharge polymerization.

The present invention provides several benefits and advantages.

One benefit of the present invention is that the vascular prosthesis of the present invention, when produced with a substantially smooth flow surface, can be exposed to flowing blood for extended time periods, as there is no cell ingrowth present on the flow surface to impede blood flow or create undesirable turbulence. The polymeric material on the luminal surface is acellular.

One of the advantages of the present invention is that the vascular prosthesis of the invention may be used to replace small, medium, and large caliber arteries in mammals; i.e., for both human and veterinary applications, and provide an improved, synthetic, blood flow passageway due to the substantially non-thrombogenic nature of the defined flow surface.

Another advantage of the present invention is that the surface of the vascular prosthesis of the invention prevents platelet deposition and prosthesis failure resulting from both gross thrombosis as well as neointimal hyperplasia.

Yet another advantage of the present invention is that, when the flow surface of the vascular prosthesis of the invention is substantially smooth, there is little blood flow resistance because graft narrowing cannot occur due to thrombus deposition or tissue ingrowth.

Still another advantage of the present invention is that the polymer lining of the vascular prosthesis of the invention increases the strength and durability of the prosthesis while not altering other desirable characteristics of the prosthesis. Also, only the luminal surface is modified. The external portion of the prosthesis is left intact to permit tissue attachment and anchoring.

A further advantage of the present invention is that the vascular prosthesis of the invention can be used with adjunctive antiplatelet or anticoagulant therapy. In addition, the vascular prosthesis of the invention is suitable for peripheral vascular surgery thereby allowing saphenous veins to be utilized in other procedures such as coronary bypass surgery. Use of the prosthesis of the invention also permits small artery reconstruction in many patients who do not have suitable saphenous veins.

Other advantages and benefits of the present invention will become readily apparent to those skilled in the art from the following description of the invention, the drawings and the appended claims.

BRIEF DESCRIPTION OF THE DRAWINGS

In drawings forming a portion of the disclosure of this invention.

DETAILED DESCRIPTION OF THE INVENTION

The present invention is directed to a vascular prosthesis and to a method of producing same. The vascular prosthesis is utilized for implantation in a living mammalian body.

A. General Discussion

The vascular prosthesis of the present invention comprises an elongated tubular segment that has a substantially foraminous, non-compliant, hollow body portion that is open at both ends. The hollow body portion has a luminal surface that defines a confined-flow passageway in the vascular prosthesis.

The luminal surface has a hydrophobic, physiologically compatible lining thereon. The lining defines a thrombus-resistant flow surface and is constituted by a polymeric material that exhibits a rate of platelet consumption of less than about $20 \times 10^8$ platelets/cm$^2$·day.

The vascular prosthesis of the present invention, in its preferred embodiment, is substantially non-compliant. As used herein, the expression "non-compliant" means showing less than 10 percent expansion of the inner diameter between systole and diastole under normal arterial pressures (less than 250 mmHg). The external surface of the vascular prosthesis permits tissue anchoring upon implantation in a human or other mammal, as is common for currently commercially available prostheses.

The tubular segment of the vascular prosthesis may be constructed of materials that exhibit the requisite strength, durability and suturability. Commercially available materials suitable for use in fabricating the prosthesis or graft include a polyester such as Dacron (C. R. Bard, Inc., Inc., Billerica, Mass.) and a polyfluorocarbon such as Teflon (Gore-Tex) (W. L. Gore, Flagstaff, Ariz.).

The lining for the tubular segment can be made from polymers that form a relatively smooth, non-polar and hydrophobic surface. Preferably, such materials are non-polar themselves; however, even polar materials can be used as long as the ultimately produced flow surface exhibits the desired surface properties.

Suitable relatively non-polar polymeric materials are those derived from repeating units of polydimethylsiloxane-methylvinylsiloxane copolymers.

Illustrative of the polydimethylsiloxanemethylvinylsiloxane copolymers are silicone elastomers, e.g., the medical grade elastomers commercially available under the designation Silastic from Dow Corning Corp., Midland, Mich. in Clean Grades Soft, Medium, and Firm. Another medical grade elastomer is available in paste form under the designation Medical Adhesive, silicone Type A from Dow Corning Corp. The Medium and Firm Grades are derived from polydimethylsiloxane copolymerized with small amounts (usually about 1 weight percent or less) of methylvinylsiloxane. The Soft Grade is derived from a copolymer of dimethylsiloxane and methylvinylsiloxane that also contains a relatively small amount of phenylmethylsiloxane whose presence contributes to the softness of the elastomer.

The above silicone elastomers exhibit a specific gravity of 1.12–1.23, a durometer hardness value of 25–75 (shore A), a tensile strength of 850–1200 pounds per square inch, and an elongation of 350–600 percent.

Among suitable relatively polar polymeric materials are the elastomeric, polyether-type polyurethanes that are physiologically compatible, i.e., free from toxic catalysts, stabilizers, processing aids or the like. Illustrative of suitable polyether-type polyurethanes are the segmented polyether polyurethanes derived from repeating units of polytetramethylene ether glycol and a mixture of methylene diisocyanate and a diamine coupler. One such material is commercially available under the designation Biomer from Ethicon, Inc., Somerville, N.J.

Biomer is a segmented polyether polyurethane polymer commercially available in various grades, usually as a 30 percent by weight solution in dimethyl acetamide. It is substantially inert in living tissue and substantially non-thrombogenic in the vascular system.

Biomer exhibits a tensile strength of 6000 pounds per square inch at an 800 percent elongation. This material has a durometer hardness value of about 75 (shore A). Other suitable commercially available polyether-based polyurethanes include Pellethane (Upjohn, Inc., Torrence, Calif.), Tygothane (Norton Chemical Co., Akron, Ohio), Superthane (Newage Industries, Willow Grove, Pa.), Renathane (Renal Systems, Inc. Minneapolis, Minn.), Minor Rubber Co. Polyurethane (Minor Rubber Co., Bloomfield, N.J.), Erythrothane (Biosearch, Inc., Raritan, N.J.), and SRI 3-2000-1-E (SRI, Menlo Park, Calif.).

In a preferred embodiment of the present invention, the lining on the luminal surface of the vascular prosthesis has a thickness of at least about 100 nanometers and less than about 1.1 millimeters with about at least about 1 micrometer to less than about 1 millimeter being a particularly preferred thickness. Such a lining provides a substantially smooth flow surface and thereby provides for minimal blood flow resistance through the prosthesis. Once the prosthesis has such a substantially non-thrombogenic lining, the prosthesis substrate is no longer recognized by the blood. The lining of the prosthesis provides thrombus resistance at normal arterial blood flow rates of at least about 50 millimeters/minute.

As used herein, "substantially smooth" means the absence of irregularities on the flow surface of the vascular prosthesis of the present invention of greater than about 5 microns in height, depth or width, except such irregularities normally associated with polymerization or extrusion processes.

In an alternative embodiment of the present invention, the polymeric lining on the luminal surface of the vascular prosthesis of the invention has a thickness of at least about 100 nanometers and less than about 1 micrometer, with a thickness of about 500 nanometers being preferred. Such a thickness provides a very thin coating of the luminal surface does not substantially alter the character, texture, or morphology of the prosthesis but only coats the fibers of the luminal surface of the vascular prosthesis. The deposited lining polymerizes around the fibers leaving the fibers themselves substantially unchanged. In this manner, thrombus deposition is reduced significantly while the initial prosthesis morphology can be maintained, if desired.

The lining of the vascular prosthesis of the present invention may also be constituted by a plurality of discrete, substantially coextensive polymeric layers. The outermost polymer layer is preferably a very thin, yet tough, highly crosslinked and flexible layer of polymer applied by means of a glow discharge that acts as a barrier against possible adsorption of lipids or other blood constituents onto the flow surface of the prosthesis. The thickness of the outermost polymer layer is preferably at least about 1 nanometer but less than about 500 nanometers. Preferred polymers for use as the outermost polymer layer are polymers having tetrafluoroethylene and hexafluroethane repeating units and that exhibit a rate of platelet consumption per unit area of $1.9 \pm 2.1$ platelets/cm$^2$·day $\times 10^8$ and $3.4 \pm 2.4$ platelets/cm$^2$·day $\times 10^8$, respectively. The hexafluoroethane may be alternatively combined with hydrogen gas and applied by means of a glow discharge, the resulting mixture when deposited as a lining exhibits a rate of platelet consumption per unit area of $2.5 \pm 3.3$ platelets/cm$^2$·day $\times 10^8$.

The substantially non-thrombogenic vascular prosthesis of the present invention is produced by a method comprising (a) depositing the above described polymeric material onto the luminal surface of the prosthesis and (b) further polymerizing the polymeric material to form a hydrophobic lining on the luminal surface.

If a relatively non-polar polymeric material is utilized, the polymeric material is dissolved in a compatible solvent to produce a solution that is then deposited onto the luminal surface. The solvent is removed by evaporation from the deposited aliquot of solution to form a polymeric residue that is cured to form a hydrophobic lining on the luminal surface. The deposition, evaporation and curing steps may be repeated successively to form a plurality of same or different polymeric layers on the luminal surface, if desired.

The above polymer-solvent solution preferably has a concentration of at least about 1 percent by weight of the polymeric material in the solvent. The upper concentration limit is the solubility of the polymeric material in the solvent. The particularly preferred concentration ranges from at least about 1 percent to about 20 percent. Suitable solvents for use in dissolving the polymeric material are organic, non-polar solvents, e.g., hexane.

If a relatively polar polymeric material is utilized, a preparation containing the polymeric material in a liquid vehicle is deposited onto the luminal surface of the tubular segment of the prosthesis. The liquid vehicle is then removed from the deposited preparation by evaporation to form a polymeric residue that is subsequently polymerized to form a hydrophobic lining on the luminal surface. These steps may be repeated successively to form a plurality of polymeric layers on the luminal surface if desired.

To form a substantially smooth polymeric layer having a thickness of at least about 1 micrometer and less than about 1 millimeter, the polymeric material is introduced into the prosthesis in a liquid or other flowable state by pouring, pushing or extrusion. For a lining thickness of less than 1 micrometer, the polymeric material usually is preferably introduced into the prosthesis as a solution.

As pointed out hereinabove, the vascular prosthesis of the invention may have a plurality of polymeric layers of different compositions that constitute the lining. In one such embodiment after one or more relatively thicker polymeric layers have been deposited, an outermost relatively thinner polymeric layer can be deposited onto the other polymeric layers by glow discharge polymerization utilizing a procedure such as that described in Yasuda, *J. Polymer Sci.*, 16, 199 (1981), the description of which is incorporated herein by reference.

Various polymeric substances have been used in making the vascular prosthesis of the present invention and their performance has been evaluated. The results are discussed below. It is to be understood, however, that the results discussed hereinbelow are illustrative of embodiments of the vascular prosthesis of the present invention and the present invention is not intended to be limited only to the specific embodiments disclosed.

B. Experiments and Results-Evaluation of Thrombogenicity

Twenty-five smooth-walled polymeric materials in tubular form were evaluated in baboons to assess their thrombogenicity. The inner diameter of these tubes ranged from 0.264–0.400 cm. These materials were studied as chronic arteriovenous shunts in baboons. These materials were not in themselves suitable as chronic artificial blood vessels since they were homogenous polymers or copolymers without a substrate graft prosthesis needed to provide the necessary suturability and handling characteristics; however, the evaluation defined those chemical properties of smooth polymers required for thrombo-resistance.

Chronic and steady-state rates of destruction of blood platelets and fibrinogen were measured. In all cases, fibrinogen utilization was minimal. The basic unit of material thrombogenicity was thus defined as the rate of destruction of platelets per cm$^2$ of material surface per day (platelets/cm$^2$·day), as determined from the rate of disappearance in vivo of autologous platelets labeled with $^{51}$Cr. The materials and methods utilized for these studies are described in Hanson et al., *J. Lab. Clin. Med.*, 95, 289 (1980) and Hanson et al., in *Biomaterials* 1980, Winter et al., eds., John Wiley and Sons, Ltd., pp. 519-530 (1982), the description of which are incorporated herein by reference. All materials were "smooth-walled" in the sense that the polymerization or extrusion processes used in their manufacture were designed to form blood-contacting surfaces free of texture, porosity, regular or irregular features.

Figure 1:
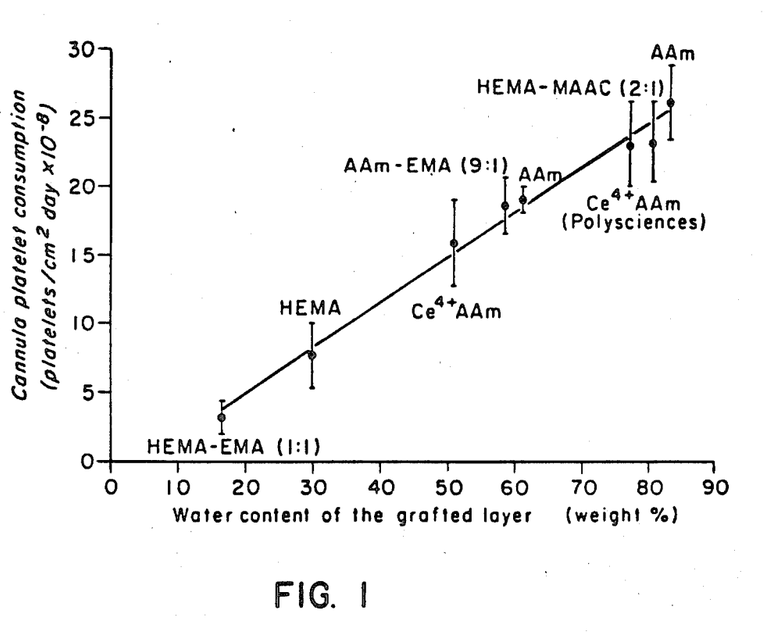
FIG. 1 is a graph illustrating the relationship of the rate of cannula platelet consumption per unit area to the graft water content of shunts grafted with eight acrylic and methacrylic polymers and copolymers. In the Figure, HEMA designates hydroxyethyl methacrylate; EMA designates ethyl methacrylate; AAM designates acrylamide; and, MAAC designates methacrylic acid. The mean values are ±1 standard error (S.E.). S.E. designates standard deviation/square root of number of observations.

Eight materials based on acrylic and methacrylic polymers or copolymers were also evaluated for comparison. These materials are considered hydrophilic and polar due to the presence of hydroxyl groups, and as these polymers readily absorb water. These materials were found to be generally thrombogenic and thus unsuitable for present purposes. Rates of platelet destruction ranged from about $4 \times 10^8$ platelets/cm$^2$·day to about $27 \times 10^8$ platelets/cm$^2$·day. Increasingly polar materials, as measured by polymer water content, were more thrombogenic, as shown in FIG. 1.

Although most of these polymers and copolymers were radiation grafted to silicone rubber polymer (Silastic) and were electrostatically neutral, it is of interest that this correlation also included one negatively charged copolymer poly(2-hydroxyethylmethacrylate)-poly(methacrylic acid), and two polyacrylamide grafts that were initiated chemically by Ce$^{4+}$ ions rather than by ionizing radiation (water contents 50.8 percent and 77.0 percent). The graft substrates for these latter materials were, respectively, Silastic pregrafted with poly(2-hydroxyethyl methacrylate) and Pellethane. Although the effects of polymer electrical charge, substrate type, and method of initiation of polymerization were not evaluated systematically, it is significant that results with the eight materials are correlated by a single variable, i.e., the water content of the grafted layer.

Four commercially available polymers, Teflon, silicone rubber (Silastic), polyvinyl chloride (Tygon), and polyethylene were also evaluated. All were found to be relatively non-polar and hydrophobic as determined by electron spectroscopy for chemical analysis, or ESCA, and known physical properties, and were also found to be substantially non-thrombogenic since all four polymers consumed less than $1.6 \times 10^8$ platelets/cm$^2$·day (versus 4-27 $\times 10^8$ platelets/cm$^2$·day for the acrylic polymers). Thus these electrostatically neutral, apolar, hydrophobic, polymer materials were observed to be far less thrombogenic than the acrylic and methacrylic polymers. The platelet consumption of these polymers evincing their non-thrombogenic properties is shown in Table I below:

TABLE I

| Platelet Consumption by Polymeric Materials | |
|---|---|
| Material | Cannula platelet consumption per unit area (platelets/cm$^2$ · day $\times 10^{-8}$)[1] |
| Polyvinyl chloride (Tygon)[2] | 0.3 ± 0.2 |
| Polyethylene (Intramedic)[3] | 0.2 ± 0.1 |
| Polydimethylsiloxane (Silastic)[4] | 1.5 ± 0.3 |
| Polytetrafluoroethylene (Teflon)[5] | 1.6 ± 1.0 |

[1]Values are mean ± 1 S.E.
[2]Tygon 550HL from Norton Co., Akron, OH.
[3]Obtained from Becton, Dickinson & Co., Parsippany, NJ.
[4]Silicone rubber from Dow Corning Corp., Midland, MI.
[5]Obtained from VWR Scientific, Inc., Seattle, WA.

Further evaluation of nine different commercial polyether urethane materials (smooth-walled "polyurethanes"), as described in Hanson et al., *J. Clin. Lab. Med.*, supra, and Hanson et al., in *Biomaterials* 1980, supra, was conducted to assess the usefulness of polyurethanes for the initial or sole polymeric layer of the prosthesis of the present invention. Although these materials are not "hydrophilic" since they absorb little water (less than about 5 percent by weight), they may be relatively "polar" or "apolar" depending primarily upon the relative proportion of hydrocarbon (C—H) or ether-type (—C—O—C—) linkages at the blood-contacting interface, as determined by ESCA spectroscopy. Rates of platelet consumption varied about 10-fold, ranging from 2.8-24.3 $\times 10^8$ platelets/cm$^2$·day, as shown in Table II below:

TABLE II

| Platelet Consumption by Polyurethanes | |
|---|---|
| Material | Platelet Consumption (plats/cm$^2$ · day $\times 10^{-8}$)[1] |
| Pellethane | 2.8 ± 0.8 |
| Biomer EB 650 | 5.2 ± 1.1 |
| Tygothane | 6.1 ± 2.0 |
| Superthane | 6.4 ± 3.4 |
| Renathane | 8.3 ± 1.7 |
| Minor Rubber Co. | 15.6 ± 4.1 |
| Biomer | 20.1 ± 1.0 |
| Erythrothane | 20.5 ± 0.8 |
| SRI 3-2000-1-E | 24.3 ± 0.8 |

[1]Mean ± S.E.

Figure 2:
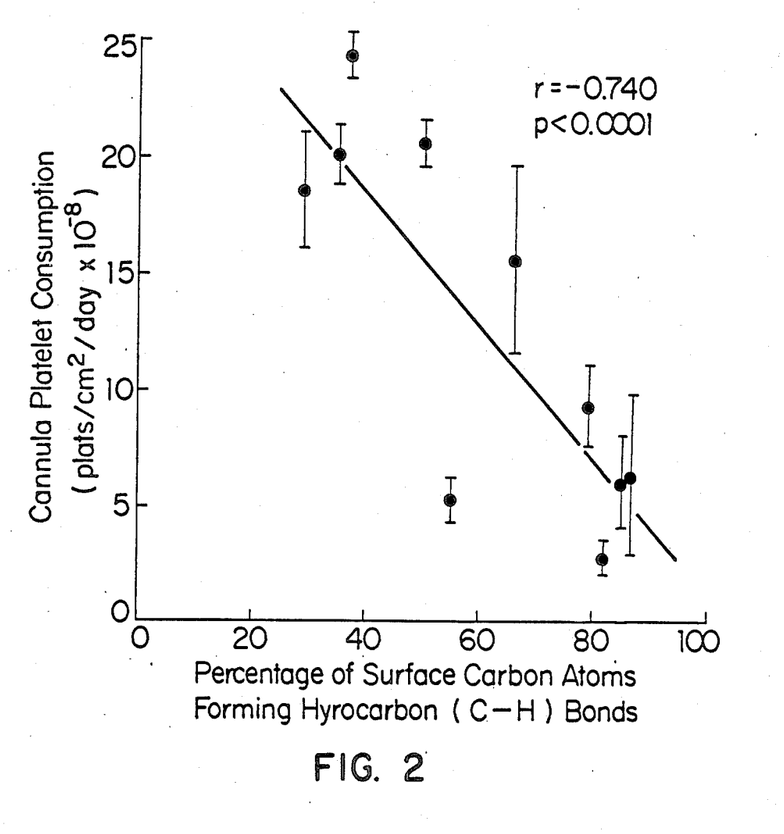
FIG. 2 is a graph illustrating platelet consumption by polyurethanes. The cannula platelet consumption per unit area is inversely related to the percentage surface carbon atoms forming C—H bonds as determined from electron spectroscopy for chemical analysis (ESCA) of polyurethane shunts. The polyurethanes screened were those commercially available under the designations SRI 3-2000-1-E, Biomer, Erythrothane, Biomer EB 650, Minor Rubber Co. Polyurethane, Renathane, Pellethane, Superthane and Tygothane. The mean values are ±1 S.E.
Figure 3:
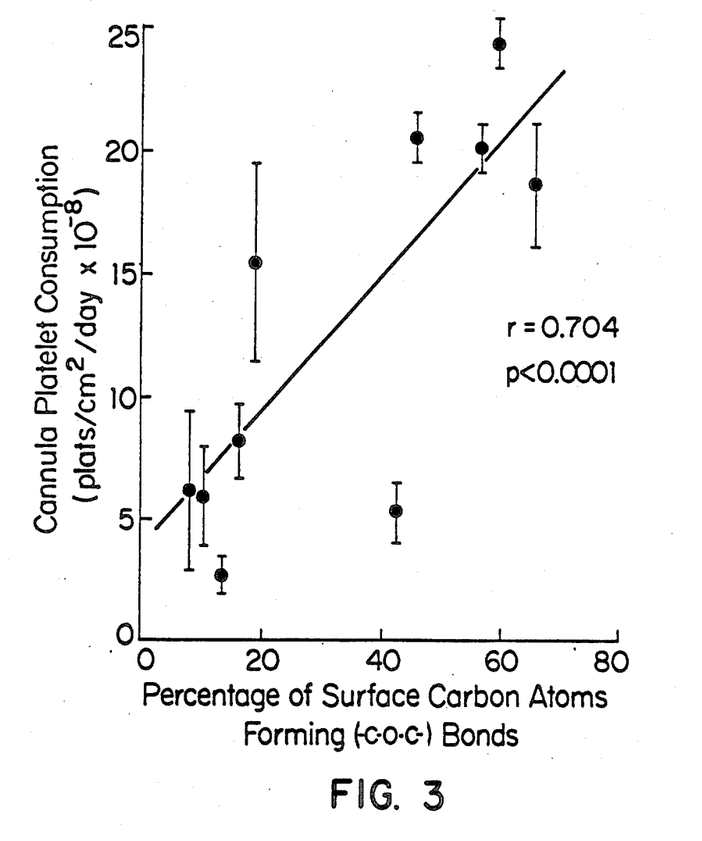
FIG. 3 is a graph further illustrating platelet consumption by polyurethanes. The cannula platelet consumption per unit area is directly related to the percentage surface carbon atoms forming —C—O—C— ether linkages as determined from ESCA of polyurethane shunts made of the same polyurethanes as in FIG. 2. The mean values are ±1 S.E.

For these polyurethanes, increasing the proportion of hydrophobic (C—H) groups conferred thrombo-resistance as evidenced by reduced platelet destruction, whereas increasing the proportion of polar (—C—O—C—) linkages at the blood-contacting surfaces resulted in increased platelet destruction. These results are shown in FIGS. 2 and 3.

It should be noted that these results were measured over the range of blood flow rates of about 50 to about 215 ml/min, that are comparable to those in a natural blood vessel.

The above results from evaluation of smooth-walled (impervious and non-porous) materials as femoral arteriovenous shunts in baboons, demonstrate that nonpolar, hydrophobic surfaces are substantially non-thrombogenic and thus suitable as lining material for the prostheses embodying the present invention.

The porosity of a vascular prosthesis is also important. Porosity has been defined as the rate at which these vascular grafts "leak" water per cm$^2$ of graft surface under 120 mmHg pressure (ml H$_2$O/min/cm$^2$)as shown in Table III below. All woven, knitted, and velour grafts are porous as defined by this measure.

TABLE III
Porosity of Commercial Vascular Grafts

| Graft Material | Graft Type | Mean Porosity (cc H₂O/min at 120 mmHg) |
|---|---|---|
| Dacron prostheses: | Woven (DeBakey) | 175 |
| | Knitted (DeBakey) | 2000 |
| | Velour (DeBakey) | 2000 |
| | Filamentous Velour (Sauvage) | 2000 |
| Teflon prostheses: | Woven (Edwards) | 40 |
| | Knitted (Edwards) | 2000 |
| | Expanded (Gore-Tex) | 0 |
| | Expanded (Impra-graft) | 0 |
| Silastic prostheses: | Replamineform | 20 micron pores 45 micron pores |
| Heterografts: | Bovine heterograft | 0 |
| | Human umbilical vein | 0 |

Although the expanded Teflon prostheses (Gore-Tex, Impra-graft) are not "porous" by this criterion, these grafts, and the silicone rubber (Replamineform) prostheses may become permeable upon wetting by blood and are designed to permit healing by vascular cell infiltration along and/or through the graft. The bovine heterograft and human umbilical vein graft are from preserved natural, non-synthetic tissues. However, until the vascular prosthesis of the present invention, no porous synthetic commercial graft was designed with a smooth, hydrophobic lining on its luminal surface to provide a non-thrombogenic surface that contacts blood flow.

Various vascular prostheses were evaluated in an arteriovenous shunt system. In order to do so, they were rendered impervious by an external coating to prevent blood leakage as described hereinafter in Section C. The following prosthesis (graft) materials were studied:

(1) Dacron grafts: 10 cm long, 4 mm i.d., external velour (Sauvage) knitted Dacron, 30 needle, uncrimped, porosity approximately 2200 ml/H₂O/cm²/min, from Bard Implants Division, C. R. Bard, Inc., Billerica, MA, Research/Lot No. 862390.

(2) Teflon grafts: expanded Teflon Gore-Tex grafts, 10 cm long, 4 mm i.d., molecular weight of 400,000–10,000,000, having a node fibral structure with a composition of 15–20 percent solids and 80–85 percent air, from W. L. Gore and Associates, Flagstaff, AZ.

(3) Silicone rubber polymer (Silastic): Medical Grade Adhesive, silicone Type A, from Dow Corning Corporation, Midland, MI.

(4) Biomer polyurethane: Biomer segmented polyether polyurethane, type: low modulus, code: E0205, Lot: 1587-227, from Ethicon, Inc., Somerville, NJ.

The vascular grafts were studied by scanning electron microscopy as described in detail in Hanson et al., *Scanning Electron Microsc.*, II, 773 (1982), the description of which is incorporated herein by reference. Grafts were incorporated into the baboon arteriovenous shunt system as described in Hanson et al., supra. The basic measure of graft thrombogenicity was the total number of platelets deposited in the period 0–3 hours following blood exposure, as determined from gamma camera imaging of the grafts following the labeling of autologous blood platelets with $^{111}$In-oxine. These methods are described hereinafter in detail in Section C.

When the Dacron grafts were placed over the 4 mm internal diameter (i.d.) Teflon rod and dipped into the unmodified silicone rubber polymer, the external graft surface became coated. After allowing the polymer to cure for 48 hours at room temperature, removal of the rod, and autoclaving, the graft was evaluated in four baboons. The results are shown in FIG. 4, wherein the silicone rubber polymer coated Dacron is referred to as "Silastic-Dacron" and the Parafilm coated Dacron is called "Uncoated-Dacron".

Figure 4:
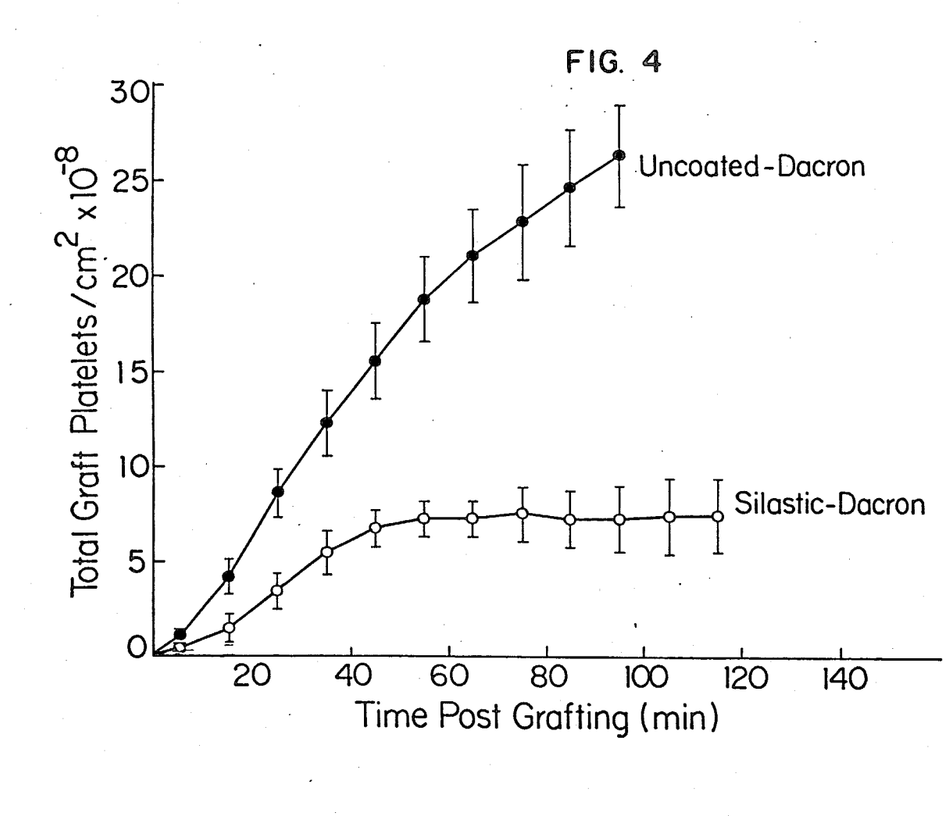
FIG. 4 is a graph illustrating the number of platelets deposited on the luminal surface of a graft in the period 0–2 hours following blood exposure. The results for a silicone rubber polymer lined polyester (Dacron) graft (prosthesis) are shown as "Silastic-Dacron" and those for a Dacron graft lined with a semi-transparent, flexible, thermoplastic (0.005 inches thick) film (Parafilm, American Can Co., New York, N.Y.) are shown as "Uncoated-Dacron."
Figure 5:
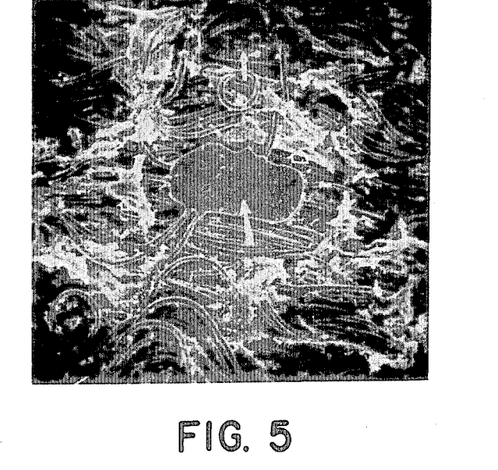
FIG. 5 is a copy of a photomicrograph of a scanning electron microgram showing the luminal surface of a graft externally lined with silicone rubber polymer and exposed to blood in a baboon for one hour ($\times 100$). Thrombus is indicated by the open arrow. Polydimethylsiloxane (Silastic)-filled fabric interstices are indicated by small closed arrows and island-like patches of Silastic by the large closed arrow.

Despite the fact that both the Parafilm and silicone rubber polymer coated the external graft surface, and that the blood reactions occured on the internal graft surface, the silicone rubber polymer coated graft showed markedly reduced platelet deposition, as shown in FIG. 4. It was subsequently determined using ESCA spectroscopy that silicone rubber polymer spontaneously coated all luminal graft Dacron fibers, while generally maintaining a luminal graft morphology that appeared unchanged. The Parafilm coated graft showed no luminal penetration of the Parafilm. A scanning electron microgram of the luminal surface of a graft externally coated with silicone rubber polymer and exposed to blood in the baboon model for one hour is shown ($\times 100$) in FIG. 5. In FIG. 5, thrombus was present (open arrows). Silastic penetrated the fabric interstices (small closed arrows) and occasionally appeared as island-like patches (large arrow), that were relatively free of thrombus.

Figure 6:
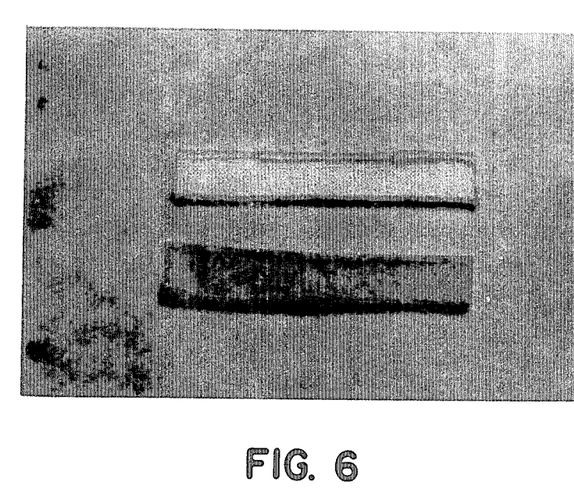
FIG. 6 is a copy of a photograph showing the coverage of luminal Dacron fibers by silicone rubber polymer as indicated by methylene blue staining. A 4.0 millimeter internal diameter (i.d.) Dacron vascular graft was lined with silicone rubber polymer (top) or Parafilm (bottom) on the external graft surface. Lining with silicone rubber polymer, but not Parafilm, prevents staining of the graft lumen by methylene blue dye indicating uniform coverage of the luminal graft fabric by silicone rubber polymer.
Figure 7:
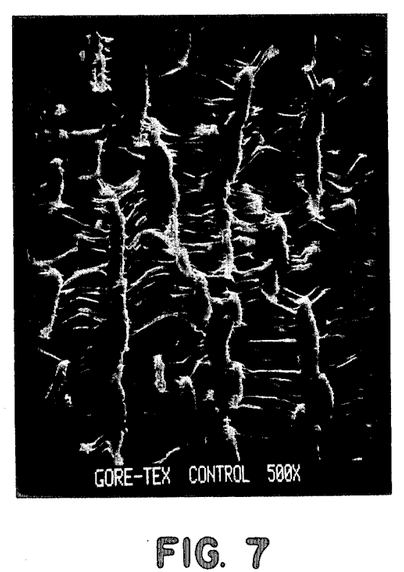
FIG. 7 is a copy of a photomicrograph of an untreated graft showing polyfluorocarbon (Teflon) (Gore-Tex, W. L. Gore, Flagstaff, Ariz.) nodules connected by Teflon Strands, or expanded Teflon. The magnification is $500\times$.
Figure 8:
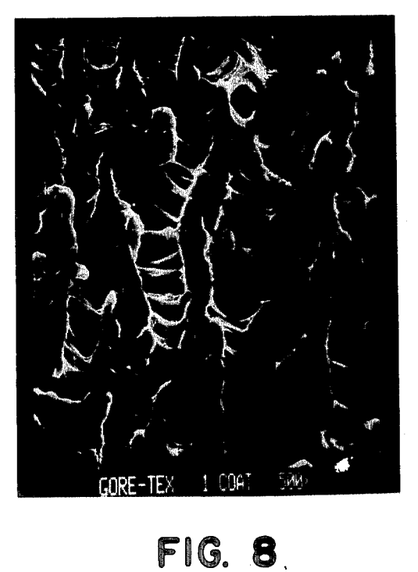
FIG. 8 is a copy of a photomicrograph ($500\times$) showing the coverage of both nodules and strands of a graft with a layer of silicone rubber polymer approximately 2 micrometers thick.
Figure 9:
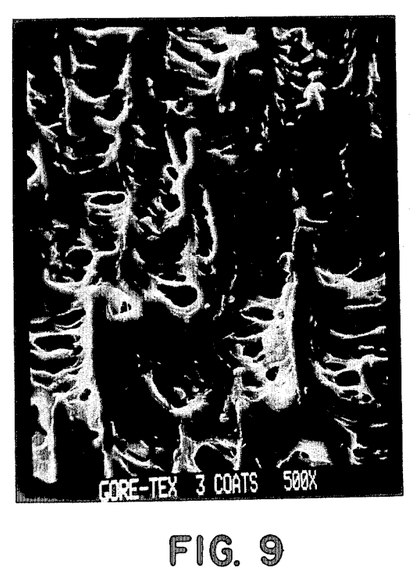
FIG. 9 is a copy of a photomicrograph (500×) showing the progressive coverage of a Teflon graft by silicone rubber polymer after three coats of the polymer.
Figure 10:
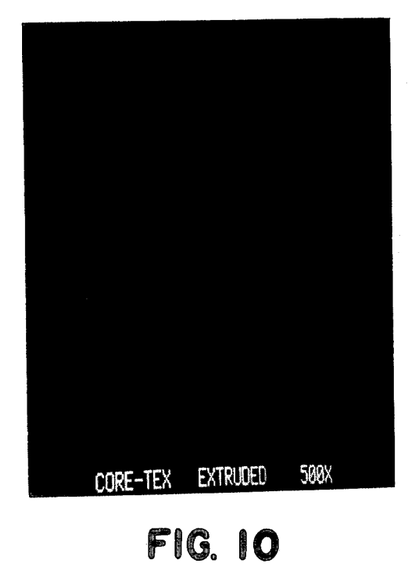
FIG. 10 is a copy of a photomicrograph (500×) showing the relatively smooth aspect of a luminal graft surface lined by extrusion with silicone rubber polymer. The occasional axial undulation is due to the extrusion process.
Figure 11:
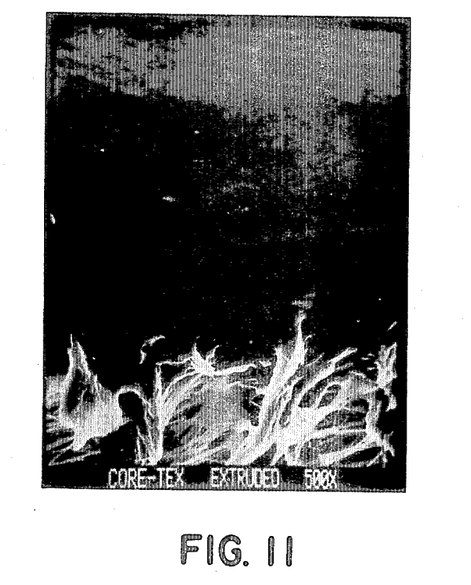
FIG. 11 is a copy of a photomicrograph (500×) showing a graft having silicone rubber polymer extruded thereon and indicating the close association of silicone rubber polymer with Teflon fibers in cross section. The thickness of the layer is about 40 micrometers.
Figure 12:
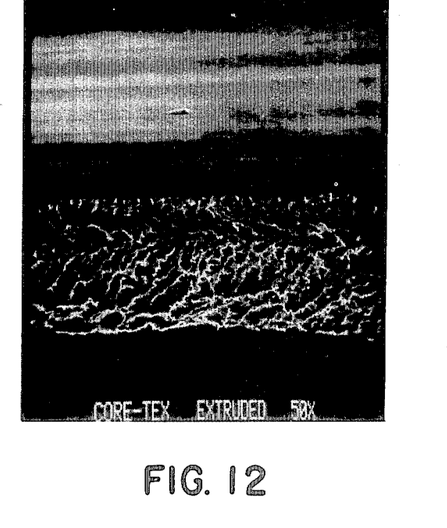
FIG. 12 is a copy of a photomicrograph (50×) of a Teflon graft extrusion lined with silicone rubber polymer. The polymer layer on the luminal surface of the graft is confined to the graft luminal interface. The graft has a "spongy" appearance.
Figure 13:
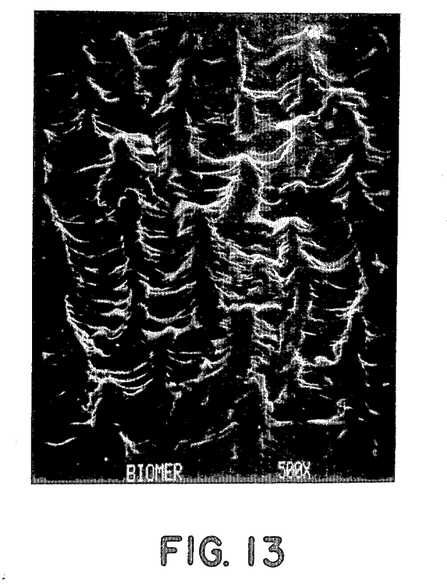
FIG. 13 is a copy of a photomicrograph (500×) of polyurethane (Biomer, Somerville, N.J.) on a Teflon graft. Liquid polymer was poured once through the graft, drained, and allowed to cure for 48 hours. The polymer lined the luminal fibers and nodules in a manner similar to silicone rubber polymer in FIG. 8.

The complete coverage of the luminal Dacron fibers by silicone rubber polymer was also demonstrated by methylene blue staining as shown in FIG. 6. Whereas the luminal fibers of Parafilm coated grafts could be stained blue, indicating unmodified Dacron, the fibers in Silastic coated grafts would not stain indicating coverage by silicone rubber polymer. The polymer film could not be removed by extensive washing with detergents. These studies indicated that contaminating films or complete surface coverage by other polymers might markedly reduce the thrombogenicity of commercial Dacron grafts.

In order to further demonstrate the improved thrombo-resistance of the vascular prosthesis of the present invention, one gram of silicone rubber polymer was dissolved in 10 grams of hexane (HPLC grade, J. T. Baker Co., Phillipsburg, N.J.) and filtered once through a 0.44 micrometer millipore filter. The solution was poured once through the graft and allowed to cure at room temperature for at least 24 hours (1 coat) or was poured through on 3 successive days (3 coats). Alternatively, undiluted silicone rubber polymer was pushed using a syringe into the lumen of the 4 mm i.d. graft and subsequently largely removed by pulling a 4 mm stainless steel bob through the graft. This resulted in a relatively smooth extruded luminal lining of silicone rubber polymer, that did not modify the external graft surface. The morphologic features of these grafts are shown in the micrographs of FIGS. 7–13.

Figure 14:
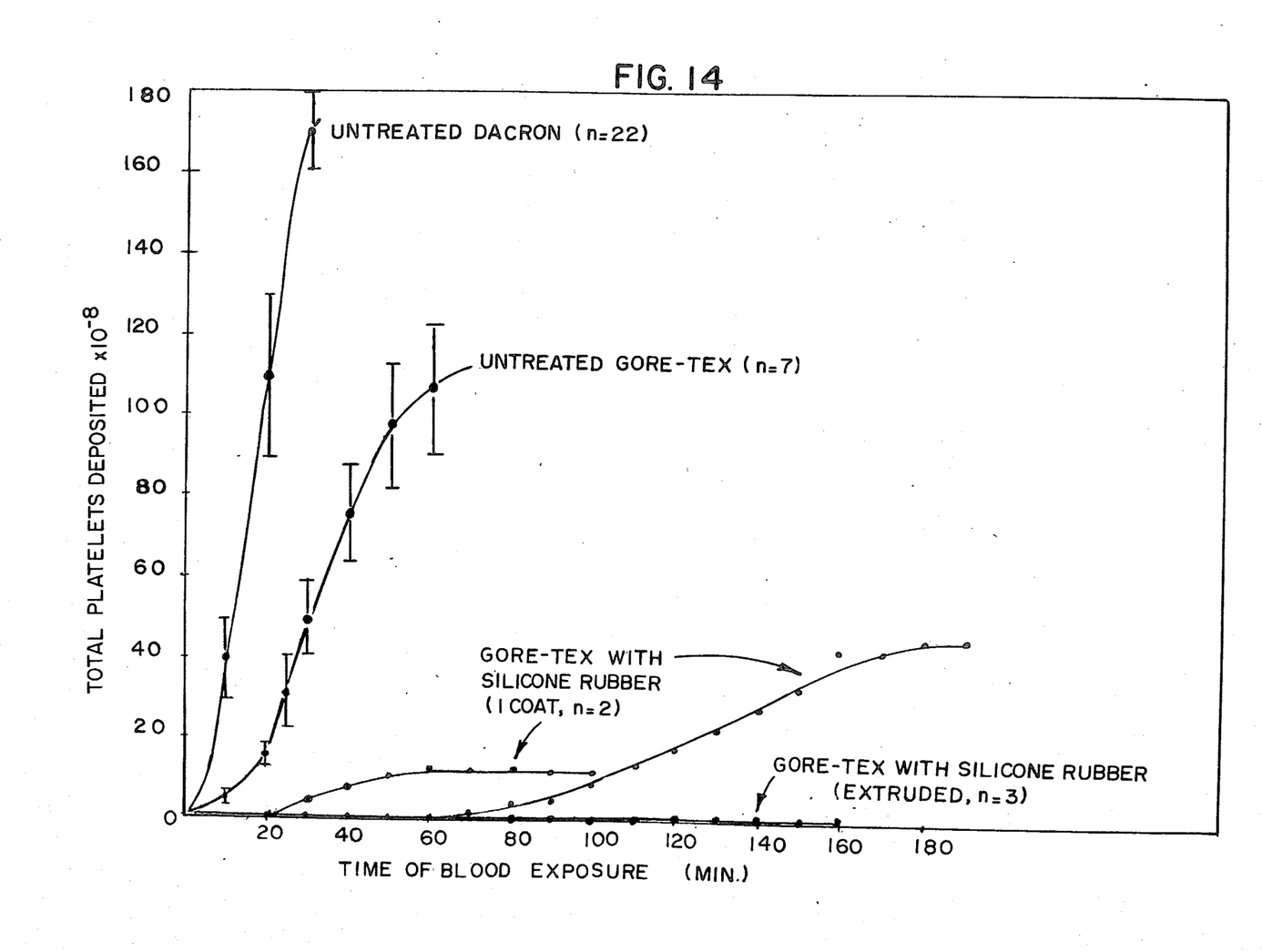
FIG. 14 is a graph illustrating the number of platelets deposited on the luminal surface of various lined or unlined grafts in the period of 0-3½ hours. All of the grafts were 10 cm×4 mm.

Both untreated Dacron and Teflon grafts were highly thrombogenic, accumulating greater than $100 \times 10^8$ platelets within 60 minutes as shown in FIG. 14. Even lightly coating Teflon with one coat of diluted silicone rubber polymer markedly reduced platelet accumulation in two evaluations. In three babbons, Teflon smoothly coated with silicone rubber polymer by the extrusion process accumulated no detectable platelets. All grafts were 10 cm×4 mm.

Figure 15:
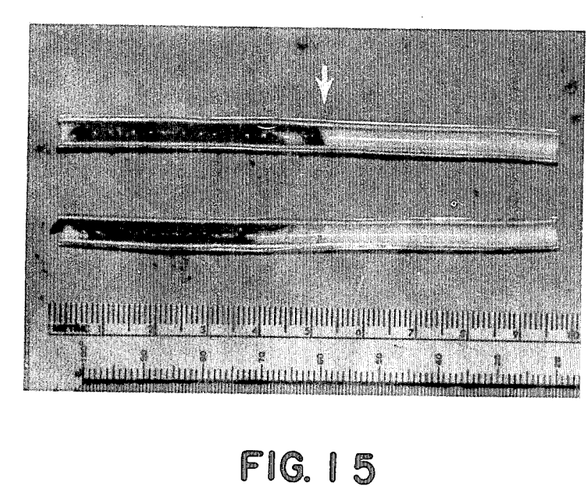
FIG. 15 is a copy of a photograph showing a Teflon graft lined smoothly on one-half with silicone rubber polymer and unlined on the other half. The 10 centimeter long, 4 millimeter internal diameter Teflon (Gore-Tex) vascular graft was exposed to flowing blood for 3 hours in a baboon arteriovenous shunt. The portion of the shunt to the right of the arrow was uniformly lined with a thin layer of silicone rubber polymer as in FIGS. 10-12. The graft to the left of the arrow was not modified in any manner, having a luminal surface morphology as shown in FIG. 7. Whereas the unmodified portion of the graft accumulated considerable blood-deposited material (thrombus), the treated portion accumulated no measurable thrombus. Blood flow (210 ml/min) was from left to right.

In one study, one half of a Teflon graft was coated smoothly by extrusion with silicone rubber polymer, the other half was not modified. After three hours in the baboon, the untreated segment had accumulated considerable thrombus. The treated segment had no visually detectable thrombus. These results are shown in FIG. 15.

Figure 16:
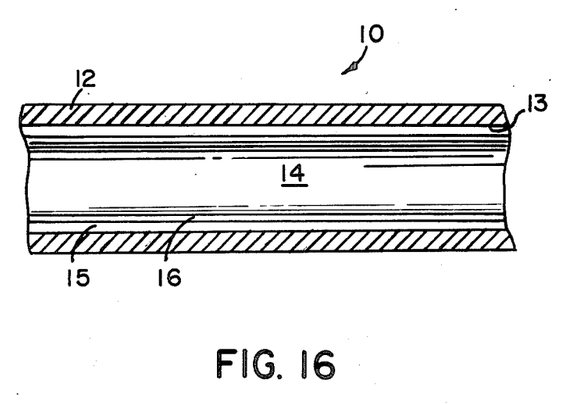
FIG. 16 shows a sectional elevation of a segment of a vascular prosthesis embodying the present invention having a plurality of polymeric layers on the luminal surface thereof.

An illustrative embodiment of the vascular prosthesis of the present invention is shown in FIG. 16. A foraminous tubular segment 10 is comprised of a hollow body portion 12 that is open at both ends. Body portion 12 has a luminal surface 13 that defines a confined-flow passageway 14. The luminal surface 13 has thereon a hydrophobic first polymeric layer 15 of a thickness of less than about 1 millimeter. Upon layer 15, a second polymeric layer 16, preferably of a thickness of less than about 500 nanometers, has been formed by glow discharge polymerization using the technique described in Yasuda, supra. Layer 16 is substantially coextensive with layer 15.

C. Experiments and Results-Gamma Camera Imaging of Vascular Grafts

Prior to evaluation in the arteriovenous shunt system, the grafts were rendered impervious to blood leakage in the following manner. First, a 4.0 mm Teflon rod (that had been thoroughly cleaned using a mild soap solution, then ethanol, and finally by rinsing with sterilized distilled water) was inserted through the graft. The graft was then externally wrapped with a 5×10 cm sheet of Parafilm and placed inside a 10 cm length of 6.3 mm i.d. "heat shrink" Teflon tubing (Small Parts Inc., Miami, Fla.).

The Teflon tubing containing the graft segment was gently heated over a low Bunsen flame until shrinkage to about 5.3 mm had occurred, resulting in a compression of the Parafilm onto the external fabric interstices without modification of the luminal graft surface. Silicone rubber tubing, 10 cm×4.0 mm i.d., was transferred onto the Teflon rod and connected to both ends of the graft segment using Silastic Medical Grade Adhesive, silicone Type A. When the polymer had cured for 24 hours, the Teflon rod was carefully pulled from the tubing lumen. This procedure produced impervious grafts rigidly constrained to a linear geometry, and having an inner diameter of 4.0 mm. The resulting isodiametric flow channel was smooth in its transition from the Silastic to the graft surface without imperfections due to the coupling procedure. The graft was connected into the baboon shunt system using blunt-edged Teflon connectors. Data obtained from grafts prepared in this manner are shown in FIGS. 4 and 14.

Autologous baboon blood platelets were labeled with $^{111}$In-oxine according to the following procedures. Whole blood (100 ml) was collected directly into plastic bags (TA-3, Fenwal Labs, Deerfield, Ill.) containing 20 ml acid-citrate-dextrose anticoagulant (NIH formula A). The blood was centrifuged in the bag at 300×g for 10 minutes. The supernatant platelet-rich plasma (PRP) was then transferred to a second bag and the pH adjusted to 6.5 by the addition of 0.15M citric acid (0.1 ml/10 ml PRP). The red blood cell fraction was returned to the donor mammal. The platelets were formed into a pellet by centrifugation of the PRP at 1300×g for 15 minutes. The supernatant platelet-poor plasma (PPP) was completely decanted and discarded.

To remove residual plasma proteins, the bag containing the platelet pellet was carefully washed once by overlaying with 30 ml of Ringer's citrate dextrose (RCD, pH 6.5) that was then decanted and discarded. The pellet was then gently resuspended in 5.0 ml RCD, and incubated for 30 minutes with 500–700 micro $Ci^{111}$-In-oxine (Amersham Corp., Arlington Heights, IL). Contaminating red cells were removed by a final slow centrifugation at 200×g for 5 minutes.

Labeling efficiency was determined by diluting 200 microliters of the labeled-platelet concentrate with 5.0 ml RCD, and comparing the activity in 0.5 ml of the diluted platelet suspension with the activity in 0.5 ml of cell-free supernatant following centrifugation at 3000×g for 30 minutes. A measured volume of labeled platelet suspension containing approximately 13 percent non-platelet bound isotope was then injected directly into the recipient mammals following the preparation of a 100 microliter standard. Additional washing procedures to remove non-platelet bound isotope were deemed undesirable since they may produce in vitro cell damage.

Circulating platelet $^{111}$In-activity was determined from 4 ml blood samples drawn prior to and following graft placement, and collected in 2 mg/ml (ethylenedinitrilo)-tetraacetic acid (EDTA). One ml of each sample was used for platelet counting, and 1.0 ml was counted for whole blood $^{111}$In activity. The remaining 2 ml were centrifuged at 3000×g for 30 minutes, and 1.0 ml of the supernatant (PPP) was counted for plasma $^{111}$In-activity. All blood and plasma samples were counted using a gamma spectrometer (Nuclear Chicago, Chicago, Ill.). Platelet counts were performed on whole blood using an electronic platelet counter (Clay Adams UF-100, Parsippany, N.J.).

Scintillation camera imaging of both gamma photon peaks of $^{111}$In (172 keV and 247 keV) has generally required high energy collimation to prevent image blurring, despite a decrease in both sensitivity and spatial resolution. Since platelet-specific activity was not a limiting factor in the present studies, a high sensitivity $^{99}$Tc collimator could be used with good resolution by imaging only the lower energy peak of $^{111}$In (172 keV peak with a 5 percent energy window). Images of the Dacron grafts, including proximal and distal Silastic segments, were acquired with a Picker DC 4/11 Dyna scintillation camera (Picker Corp, Northford, CT) and stored on and analyzed by a Medical Data System SIMUL computer (Medtronic, Ann Arbor, MI) interfaced with the camera. This system permitted simultaneous acquisition and analysis of data in 64×64 word mode and was used to generate the data shown in FIGS. 4 and 14. Immediately prior to imaging the graft segments ex vivo, 2 minute images were acquired of the 200 microliter sample of platelet concentrate (injection standard) and of 4.0 mm i.d. Silastic tubing filled with autologous blood and having the same luminal volume as the graft segment (blood standard).

All standards and tubings were placed into a groove precisely machined into plexiglass to maintain a linear geometry that was positioned approximately 1 cm from the face of the collimator. The activities of the standards and 10 cm graft segments were counted in the same 3.1 cm×12.5 cm region of interest (10×40 pixels) as defined by image analysis software routines. From the time of graft placement, images were acquired continuously with data storage at 2 minute intervals. Deposited $^{111}$In-platelet activity was calculated by subtracting the blood standard activity from all dynamic study images.

Grafts were placed and imaged sequentially for several days following injection of a single preparation of $^{111}$In-labeled platelets. Since circulating $^{111}$In-platelet activity was lost continuously through normal physiologic mechanisms, and acutely by serial graft placement, measurements of platelet accumulation were expressed as a graft/blood ratio, defined as the ratio of deposited graft activity divided by the whole blood (circulating) platelet activity within the graft lumen measured at the beginning of each evaluation. This measurement was chosen since it is independent of the size of the mammal, the amount of isotope injected, or the extent to which the isotope may have decayed, Ritchie et al., *Am. J. Cardiol.*, 47, 882 (1981); Callow et al., *Ann. Surg.*, 191, 362 (1980). The graft/blood ratio, however, depends upon the timing or sequence of observations if platelet functional alterations occur as a result of aging in the circulation or repeated exposure to thrombogenic surfaces.

To determine the graft/blood ratio, the activity of blood within the graft lumen (1.26 ml) was determined by two separate methods. First, it was calculated directly after imaging the blood standard (1.57 ml blood volume). In the second method, the activity per ml of blood present at the beginning of each experiment was calculated by imaging the injection standard prior to each experiment, multiplying this value by the CPM per ml of whole blood drawn at the time of the experiment (as determined using a gamma counter at some later time $t_j$), and dividing by injection standard activity (also measured in the gamma counter at $t_j$) All blood samples and standards were counted simultaneously at the end of each series of evaluations. In all calculations, radioactivity values refer to platelet activity only, with total blood and standard values having been corrected for the fraction of non-platelet isotope.

Total platelet deposition (labeled plus unlabeled cells) was estimated by multiplying the graft/blood ratio by the factor: graft blood volume (1.26 ml)×platelet concentration per ml of whole blood. This computation involved the assumption that the labeled and unlabeled platelet populations were equivalent with respect to graft deposition at all times. Values for total platelet deposition onto the vascular grafts as determined by the above method are shown in FIGS. 4 and 14.

The foregoing demonstrates that the vascular prosthesis of the present invention provides a substantially non-thrombogenic flow surface for contact with blood flow in a mammalian body. The thrombus-resistance is imparted to the vascular prosthesis of the invention by the novel hydrophobic, polymeric lining on the luminal surface of the vascular prosthesis.

The foregoing is intended as illustrative of the present invention but not limiting. Numerous variations and modifications may be effected without departing from the true spirit and scope of the invention.

What is claimed is:

1. A vascular prosthesis for implantation in a living mamalian body comprising (a) an elongated tubular segment, said tubular segment having a substantially foraminous, non-complaint, hollow body portion open at both ends, said hollow body portion having a luminal surface defining a confined-flow passageway, and (b) a hydrophobic, physiologically compatible lining constituted by a polymeric material on said luminal surface and defining a thormbus-resistant flow surface that prevents platelet deposition and is free from surface irregularities greater than about 5 microns in height, depth or width, said polymeric material exhibiting a rate of platelet consumption of less than about $20 \times 10^8$ platelets/cm$^2$. day.

2. The vascular prosthesis of claim 1 wherein said flow surface is thrombus-resistant at an arterial blood flow rate of at least about 50 millimeters/minute.

3. The vascular prosthesis of claim 1 wherein said polymeric material is made up of a polymer principally constituted by repeating units of a polyether-based polyurethane.

4. The vascular prosthesis of claim 3 wherein said polyether-based polyurethane is derived from a polytetramethylene ether glycol and a mixture of methylene diisocyanate and a diamine coupler.

5. The vascular prosthesis of claim 1 wherein said polymeric material is made up of a silicone elastomer.

6. The vascular prosthesis of claim 15 wherein said silicone elastomer is principally constituted by repeating units of polydimethylsiloxane-methylvinylsiloxane copolymer.

7. The vascular prosthesis of claim 1 wherein said lining is constituted by a plurality of discrete, substantially coextensive polymeric layers.

8. The vascular prosthesis of claim 7 wherein the outermost polymeric layer of said lining is made up of a polymer principally constituted by repeating units of tetrafluoroethylene.

9. The vascular prosthesis of claim 7 wherein the outermost polymeric layer is made up of a polymer principally constituted by repeating units of hexafluoroethane.

10. The vascular prosthesis of claim 1 wherein said rate of platelet consumption is in a range of about $2.0 \times 10^8$ platelets/cm$^2$·day to about $20 \times 10^8$ platelets/cm$^2$·day.

11. The vascular prosthesis of claim 1 wherein said rate of platelet consumption is in a range of about $1.2 \times 10^8$ platelets/cm$^2$·day to about $1.8 \times 10^8$ platelets/cm$^2$·day.

12. A vascular prosthesis of claim 1 wherein said lining has a thickness of at least about 100 nanometers and less than about 1.1 millimeters.

13. The vascular prosthesis of claim 12 wherein said lining has a thickness of at least about 1 micrometer and less than about 1 millimeter 14. The vascular prosthesis of claim 12 wherein said lining has a thickness of at least about 100 nanometers and less than about 1 micrometer.

15. A method of producing a vascular prothesis having a luminal surface, comprising the steps of:
(a) depositing a hydrophobic, physiologically compatible polymeric material exhibiting a rate of platelet consumption of less than about $20 \times 10^8$ platelets/cm$^2$·day onto said luminal surface as a layer having a thickness of at least about 100 nanometers to less than about 1.1 millimeters; and,
(b) further polymerizing the deposited polymeric material to form a substantially smooth hydrophobic lining on said luminal surface free from surface irregularites greater than about 5 microns in height, depth or width.

16. The method of claim 15 wherein:
(a) said polymeric material is dissolved in a compatible solvent to produce a solution having a polymeric material concentration in the range of about 1 percent by weight to about 20 percent by weight based on the weight of the solvent;
(b) said solution is deposited onto said luminal surface;
(c) said solvent is removed by evaporation from said deposited solution to form a polymeric residue; and
(d) said polymeric residue is cured to form a substantially smooth hydrophobic lining on said luminal surface free from surface irregularities greater than about 5 microns in height, depth or width.

17. The method of claim 16 wherein said lining is derived from a silicone elastomer.

18. The method of claim 17 wherein said silicone elastomer is principally constituted by repeating units of polydimethylsiloxane.

19. The method of claim 16 wherein said solution has a concentration of from about 1 percent to about 20 percent by weight of said polymeric material in said solvent.

20. The method of claim 16 wherein said solvent is an inert, organic, non-polar solvent.

21. The method of claim 20 wherein said solvent is hexane.

22. The method of claim 16 wherein said steps (b)–(d) are repeated successively to form a plurality of discrete polymeric layers.

23. The method of claim 16 including the further step of depositing a polymeric layer defining a flow surface by glow discharge polymerization.

24. The method of claim 23 wherein said polymeric layer is derived from tetrafluoroethylene.

25. The method of claim 23 wherein said polymeric layer is derived from hexafluoroethane.

26. The method of claim 15 further including the steps of:
(a) depositing a preparation containing said polymeric material in a liquid vehicle onto said luminal surface;
(b) removing said liquid vehicle by evaporation from said preparation to form a polymeric residue; and,
(c) polymerizing further said polymeric residue to form a hydrophobic lining on said luminal surface.

27. The method of claim 26 wherein said lining is derived from a polymeric material made up of a polymer principally constituted by repeating units of a polyether-based polyurethane.

28. The method of claim 27 wherein said polyether-based polyurethane is derived from a polytetramethylene ether glycol and a mixture of methylene diisocyanate and a diamine coupler.

29. The method of claim 26 wherein said steps (a)–(c) are repeated succesively to form a plurality of discrete polymeric layers.

30. The method of claim 26 including the further step of depositing a polymeric layer defining a flow surface by glow discharge polymerization.

31. The method of claim 30 wherein said polymeric layer is derived from tetrafluoroethylene.

32. The method of claim 30 wherein said polymeric layer is derived from hexafluoroethane.

* * * * *

UNITED STATES PATENT AND TRADEMARK OFFICE
CERTIFICATE OF CORRECTION

PATENT NO. : 4,687,482
DATED : August 18, 1987
INVENTOR(S) : Stephen R. Hanson

It is certified that error appears in the above-identified patent and that said Letters Patent is hereby corrected as shown below:

Column 1, after the heading "DESCRIPTION" and before the heading "Technical Field", insert the following paragraph:

--This invention was made with government support under Contract No. AI 17699 awarded by the National Institutes of Health. The government has certain rights in the invention.--

Signed and Sealed this

Fourth Day of January, 1994

Attest:

BRUCE LEHMAN

Attesting Officer

Commissioner of Patents and Trademarks